US006136536A

United States Patent [19]
Tomkinson et al.

[11] Patent Number: 6,136,536
[45] Date of Patent: Oct. 24, 2000

[54] RAPID GENERATION OF STABLE MAMMALIAN CELL LINES PRODUCING HIGH LEVELS OF RECOMBINANT PROTEINS

[75] Inventors: Kathleen Tomkinson, Cambridge; Monique Davies, Arlington; John McCoy, Reading, all of Mass.

[73] Assignee: Genetics Institute, Inc., Cambridge, Mass.

[21] Appl. No.: 09/175,690

[22] Filed: Oct. 20, 1998

Related U.S. Application Data

[60] Provisional application No. 60/063,449, Oct. 29, 1997.

[51] Int. Cl.[7] .......................... C12N 15/00; A61K 48/00; C12Q 1/68
[52] U.S. Cl. ............................ 435/6; 435/69.1; 435/91.1; 435/91.4; 435/325; 435/352; 435/358; 536/23.1; 536/24.1
[58] Field of Search .............................. 435/6, 91.1, 91.4, 435/325, 352, 358, 320.1, 476; 536/23.1, 24.1

[56] References Cited

U.S. PATENT DOCUMENTS

| | | | |
|---|---|---|---|
| 4,740,461 | 4/1988 | Kaufman | 435/69.1 |
| 5,464,758 | 11/1995 | Gossen et al. | 435/69.1 |
| 5,770,425 | 6/1998 | Anderson et al. | 435/226 |
| 5,858,704 | 6/1999 | Grinnell | 435/69.1 |
| 6,004,941 | 12/1999 | Bujard et al. | 514/44 |

FOREIGN PATENT DOCUMENTS

| | | |
|---|---|---|
| wO 94/16075 | 7/1994 | WIPO . |
| WO 94/23048 | 10/1994 | WIPO . |
| WO 94/29442 | 12/1994 | WIPO . |
| WO 96/01313 | 1/1996 | WIPO . |
| WO 97/35992 | 10/1997 | WIPO . |

OTHER PUBLICATIONS

Shockett et al., PNAS 92 : 6522–6526, Jul. 1995.
Kim et al., J. of Virology 69(4) p. 2565–2573, Apr. 1995.
Magalini et al., DNA and Cell Bio. 14(8) p. 665–671, Nov. 1995.
Langer et al., Virology 221 : 172–179, Jul. 1995.
M. Gossen and Hermann Bujard, "Tight control of gene expression in mammalian cells by tetracycline–responsive promoters," *Proc. Natl. Acad. Sci.,* vol. 89, pp. 5547–5551, Jun. 1992.
S.K. Jang et al.,"Initiation of Protein Synthesis by Internal Entry of Ribosomes into the 5'Nontranslated Region of Encephalomyocarditis Virus RNA in Vivo," *J. Virol,,* vol. 63, No. 4, pp. 1651–1660, 1989.
Hofmann et al., "Rapid Retroviral Delivery of Tetracycline–Inducible Genes in a Single Autoregulatory Cassette," *Proc. Natl. Acad. Sci. USA,* 93(11): 5185–5190 (1996).

*Primary Examiner*—David Guzo
*Assistant Examiner*—Melissa Schmidt

[57] ABSTRACT

Disclosed are methods, DNA sequences, vectors and cell lines useful for the rapid generation of stable mammalian cell lines expressing high levels of recombinant proteins.

21 Claims, 15 Drawing Sheets

Transfect pHTop-X into CHO transactivator cell line (CHO/A2)
↓ 2 days

Split cells into selection (.02, .05, 0.1μM MTX)
↓ 2 weeks

Pick clones into 24-well plates
↓ 1-2 weeks

Screen clones to determine level of expression
   Western
   ELISA
   Radiolabel
   Activity assay

FIG. 12

| PROTEIN | mIgG2a ELISA(ug/ml) |
|---|---|
| mCD28/mIgG2a | |
| clone# 1 | 6.8 |
| 2 | 8.6 |
| 3 | 6.9 |
| mB7.2/mIgG2a | |
| clone# 1 | 3.1 |
| 2 | 2.4 |
| 3 | 2.2 |
| mCTLA4/mIgG2a | |
| clone# 1 | 6.1 |
| 2 | 13.4 |
| 3 | 13.2 |

FIG. 14

RAPID GENERATION OF STABLE MAMMALIAN CELL LINES PRODUCING HIGH LEVELS OF RECOMBINANT PROTEINS

This application claims the benefit of U.S. Provisional application Ser. No. 60/063,449, filed on Oct. 29, 1997.

FIELD OF THE INVENTION

The present invention relates to a novel method of generating stable mammalian cell lines which produce high levels of recombinant proteins, and to the cell lines and vectors which are suitable for use in such method.

BACKGROUND OF THE INVENTION

Mammalian cell lines, such as Chinese hamster ovary (CHO) cell lines, are often used for the production of recombinant proteins. In such methods, it is desirable to generate stable cell lines and to be able to generate such high-producing stable cell lines in a relatively short period of time. The generation of such cell lines enables the rapid production of quantities of recombinant protein on a scale useful for purposes of biological evaluation and commercial production.

SUMMARY OF THE INVENTION

The present invention relates to novel mammalian expression vectors which allow the establishment in a relatively rapid period of time, preferably as short as about 4 weeks, stable mammalian cell lines producing high levels of secreted and membrane-bound recombinant proteins. In a preferred embodiment of the invention, the mammalian cell lines are of Chinese hamster ovary (CHO) origin particularly a strain negative for the dihydrofolate resistance gene (DHFR).

In one embodiment, the present invention comprises recombinant DNA sequences and gene expression plasmids useful for the generation of stable cell lines. Preferred embodiments comprise the recombinant DNA sequences of the gene expression plasmids pHTOP or pHTOP6. In other embodiments, the invention comprises recombinant DNA vectors comprising a gene encoding a chimeric transcription factor [tTA], which tTA may comprise a fusion of an *E. coli* tetracycline repressor protein [tet R] to a transcriptional activation domain of herpes simplex virus 16 (VP16); and a vector comprising a minimal promoter preceded by multiple tet operator [tet O] sequences.

The pHTop vector when transfected into the CHO/A2 cell line leads to very efficient expression of a gene cloned into it, as well as that of DHFR present on the same polycistronic message. Using a stringent MTX selection protocol, high-expressing clones can be isolated and expanded in one month. For five genes tested, expression levels are higher than COS transient expression levels. Expression levels can be amplified by growing cells in increasing concentrations of MTX. It has been demonstrated that stability of expression can be maintained for at least three weeks in the absence of selection.

The level of expression achieved through the one-step selection protocol varies from gene to gene. Secreted protein levels ranging from 1–14 µg/ml have been observed. Stringent MTX selection generally produces clones expressing uniform levels of protein, eliminating the need to screen large numbers of clones. Both secreted and membrane proteins can be expressed at high levels using the pHTop vector.

The streamlined protocol for establishing CHO stable cell lines described in the present invention can be used as an alternative to large-scale COS transfections. CHO cells grow well in serum-free media and conditioned media is easily generated for purification of novel proteins, for example, such protocol may accelerate the generation of stable cell lines in search of a function.

Figure 1:
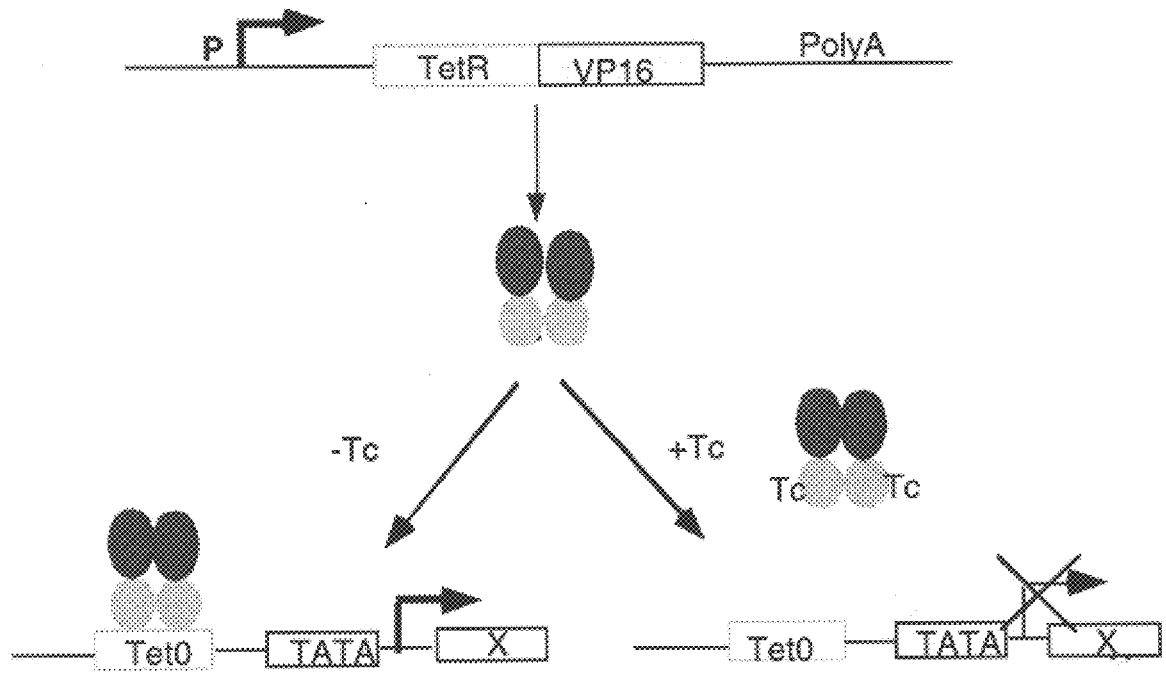
FIG. 1 is a diagram of the regulatable expression system characterized by Gossen and Bujard). This expression system is based on two elements: a chimeric transcription factor (tTA), which is a fusion between the *E. Coli* tetracycline repressor (tetR) and the transcriptional domain of herpes simplex virus 16 (VP16); and a vector in which a minimal promoter providing a TATA box is preceded by multiple tet operator (tetO) sequences. When the chimeric transactivator is expressed, its tetR domain binds to the tetO sequence. This, in turn, brings the strong activation domain VP16 in proximity to the basal transcription complex and activates it. This interaction can be reversed through the action of tetracycline (Tc) which can therefore be used as a switch to turn transcription "off." In the absence of tetracycline, expression is "on."
Figure 2A:
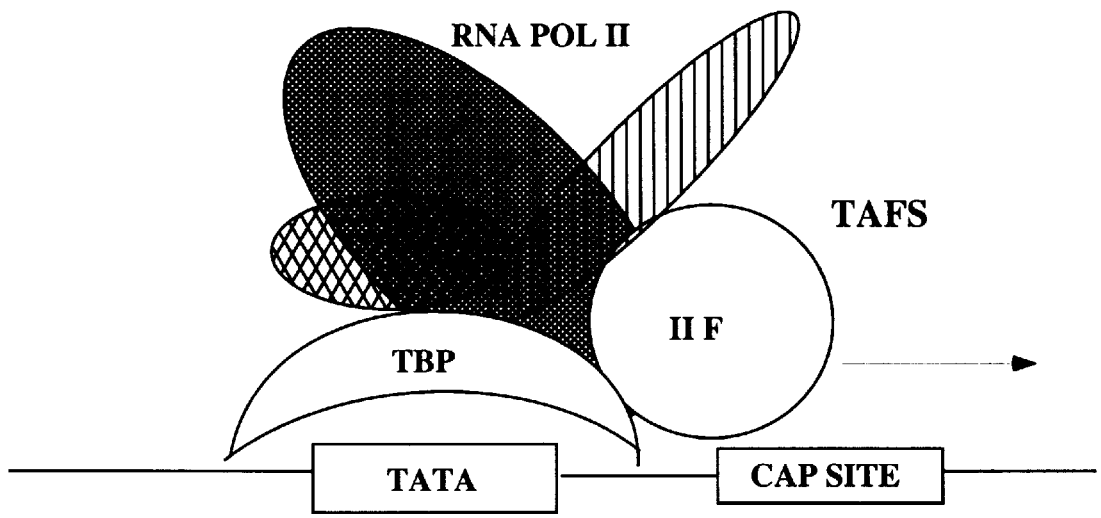
FIG. 2a is a diagram showing the basal initiation complex with the minimal promoter in the expression system.
Figure 2B:
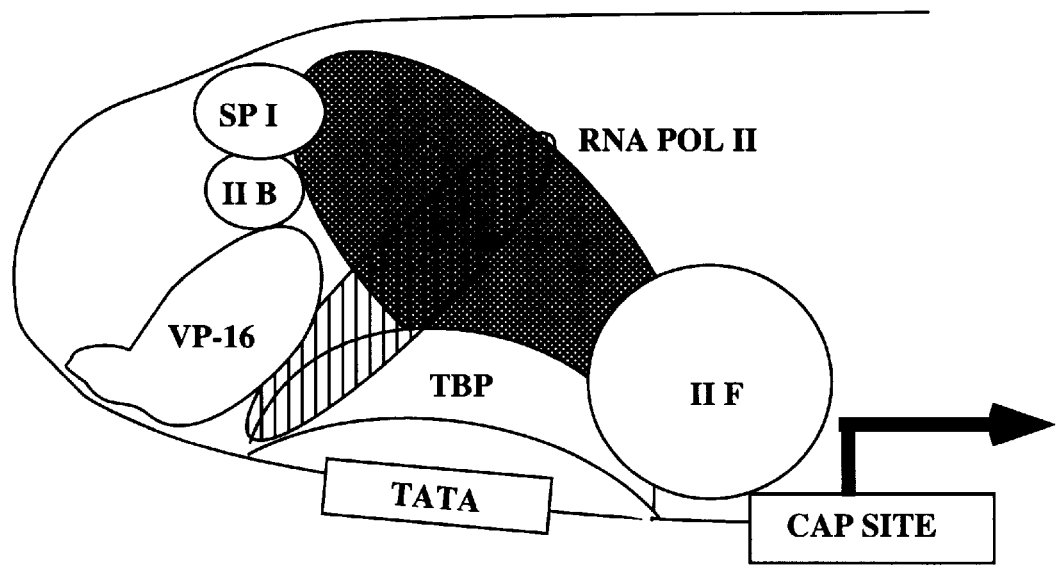
FIG. 2b shows the activated initiation complex.
Figure 3:
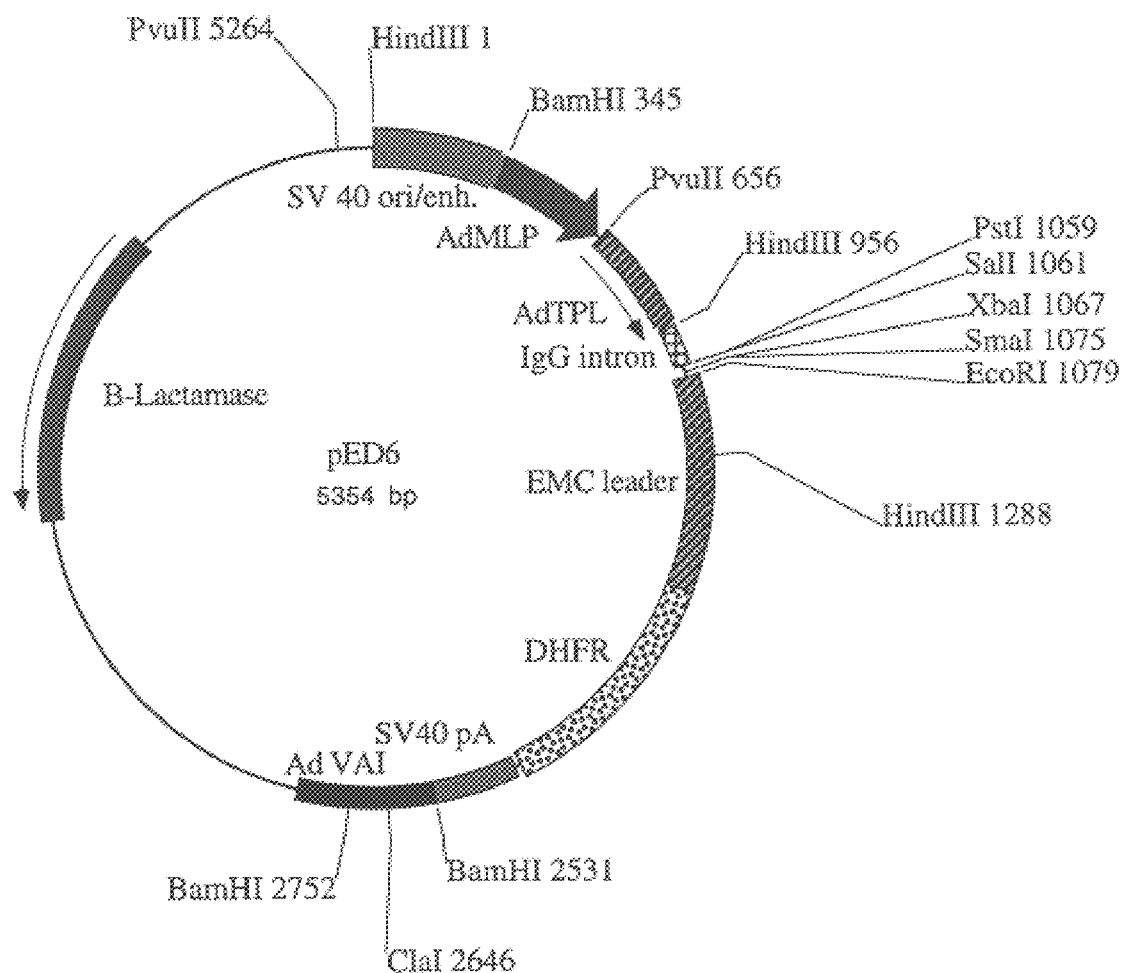
FIG. 3 is a plasmid diagram of pED6. PED6 is a plasmid of 5354 base pairs, containing the SV40 orgin of replication and enhancer, the Adenoviral Major late promoter, a hybrid intron, polylinker, EMCV leader, DHFR and SV40 early polyadenyletion region.
Figure 4:
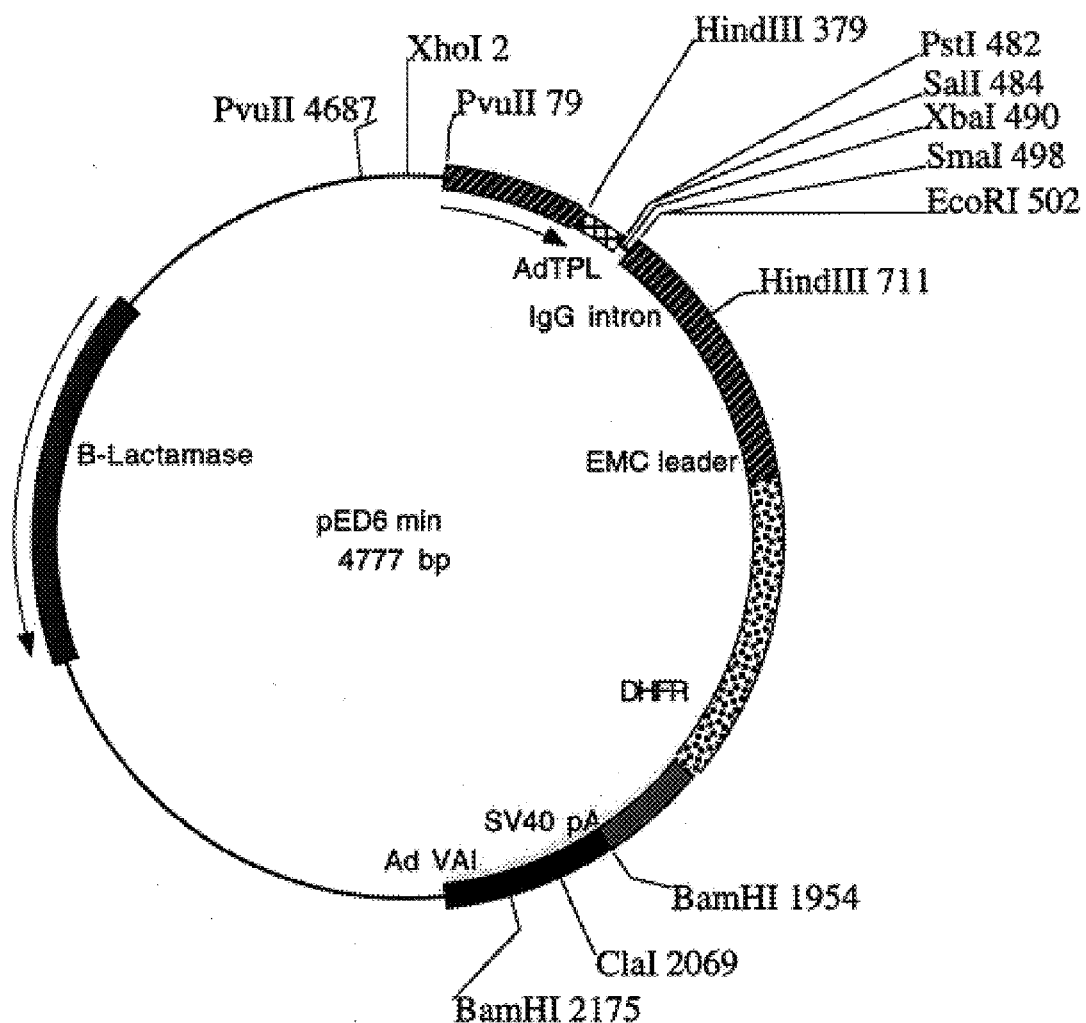
FIG. 4 is a plasmid diagram demonstrating the construction of a minimal AdMLP expression plasmid [pED6 min]. The SV40 origin and enhancer, as well as the Adenoviral major late promoter up to 8 bp from the TATA box have ben looped out of pED6, a 575 bp deletion. A unique XhoI site is inserted to allow for the insertion of tetO.
Figure 5:
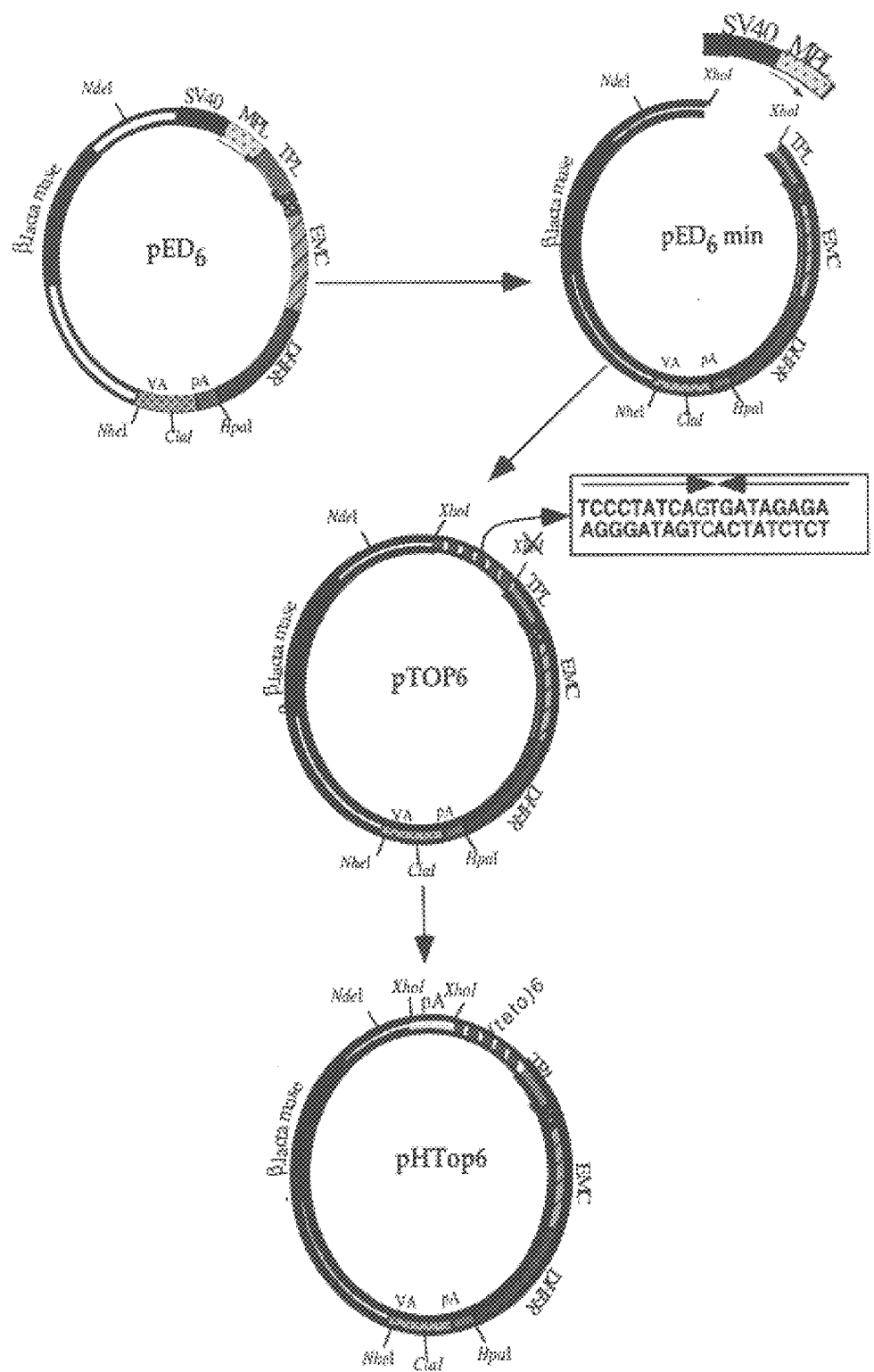
FIG. 5 is a diagram showing the construction of pHTop6 from pED6. Following the construction of pED6min, 6 tetO sequences are ligated into the XhoI site to form pTOP6. Next the HBV poly A sequences are inserted upstream of the tetO sequences. The sequence shown in FIG. 5 corresponds to nucleotides 642–660 of SEQ ID No: 1.
Figure 6:
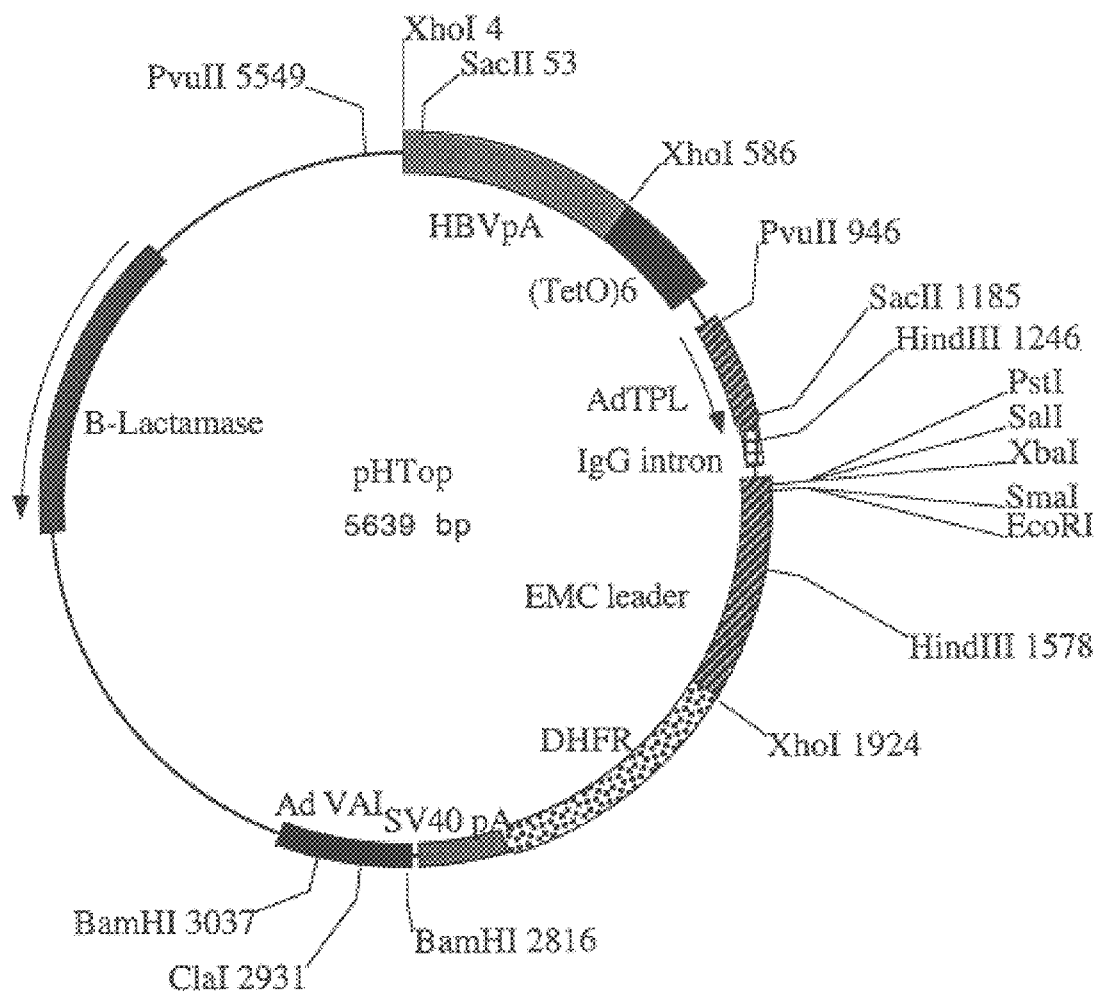
FIG. 6 is a plasmid diagram of pHTOP. pHTOP is a 5639 bp plasmid in which the EMC leader/DHFR junction of pHTOP6 is changed to 'cripple' DHFR translation without affecting the level of expression of the upstream gene. This allows the maintenance of stringent selection without the use of high levels of methotrexate [MTX].
Figure 7:
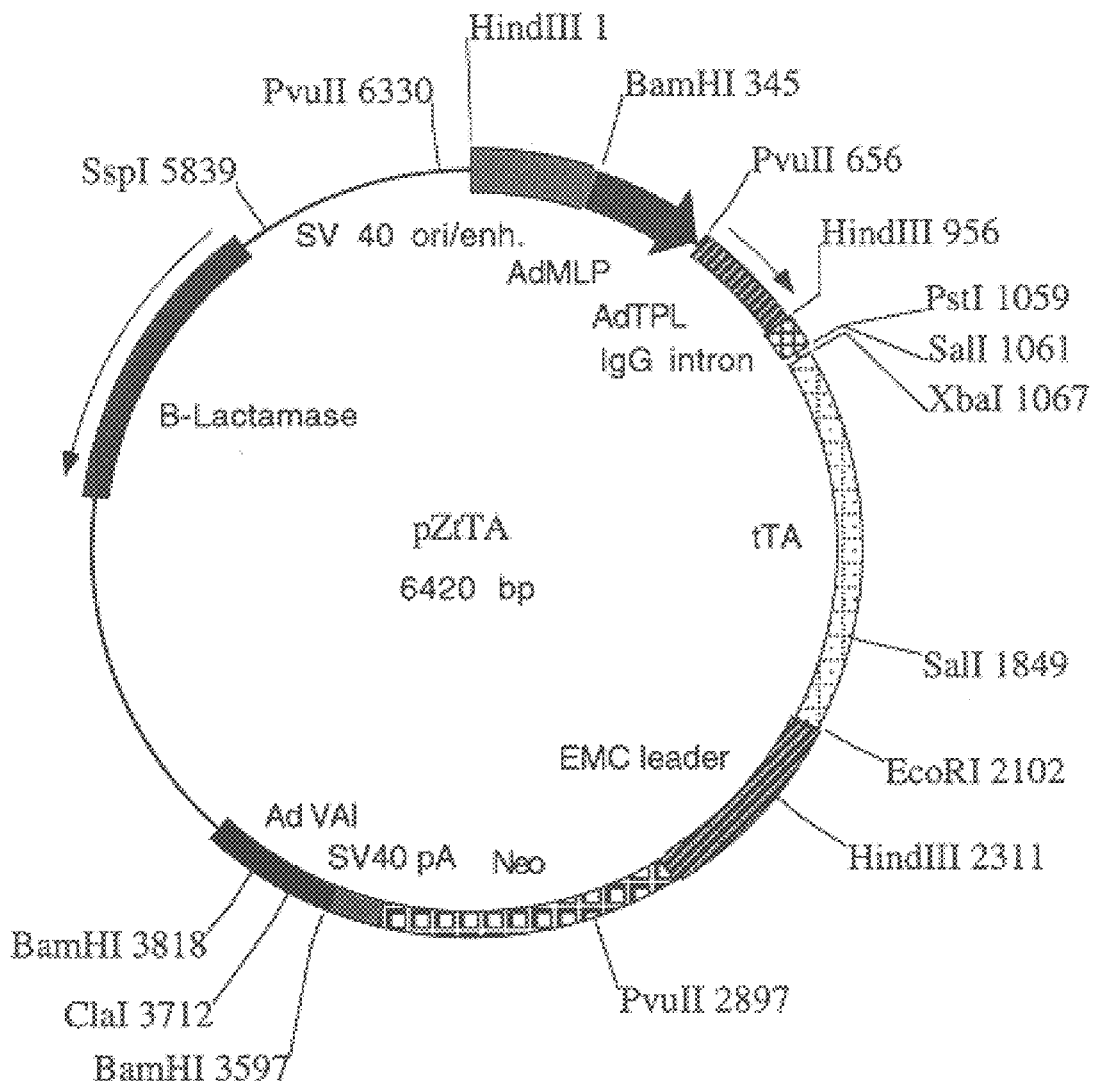
FIG. 7 is a plasmid diagram of pZtTA. pZtTA is a 6420 bp plasmid which is used to construct a transactivator CHO cell line.
Figure 8:
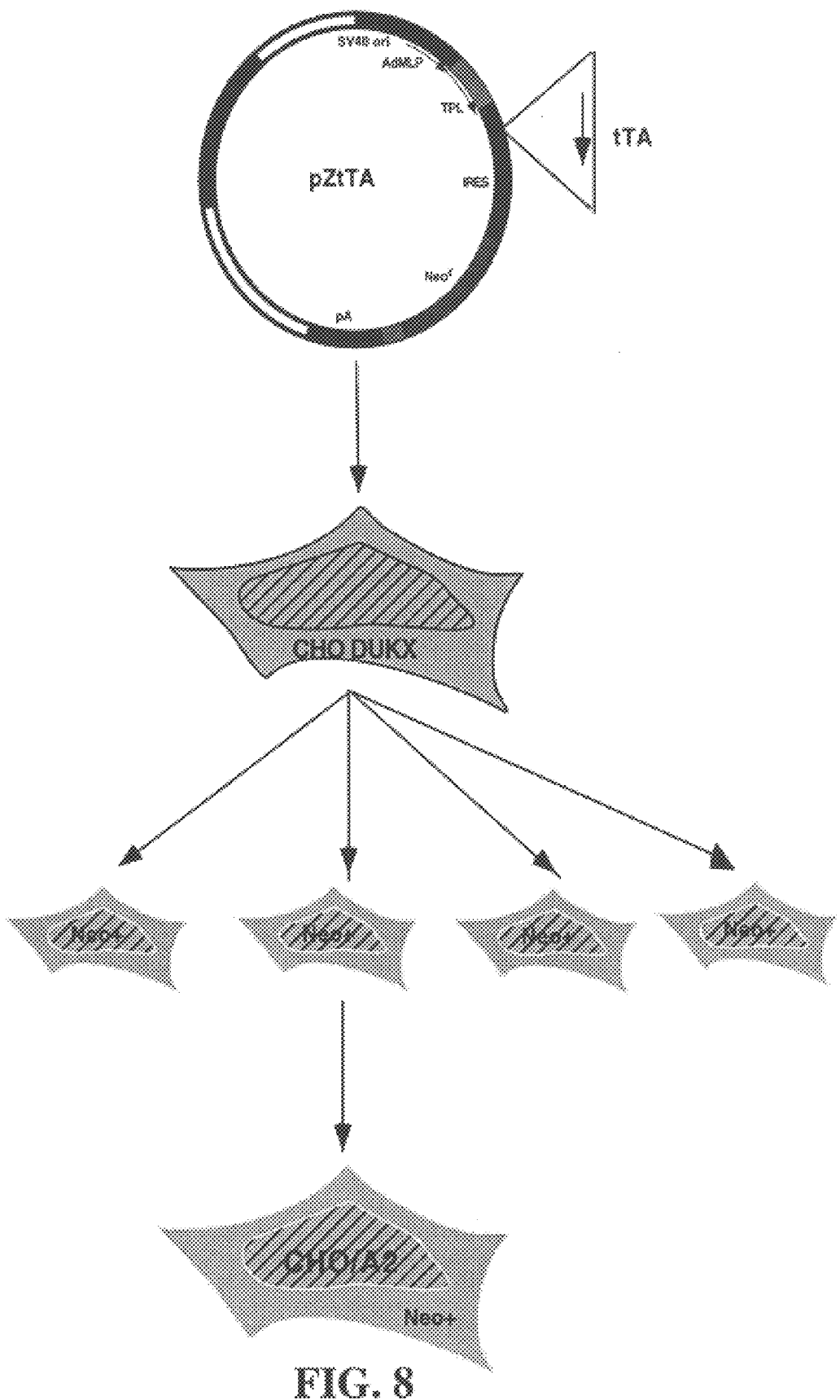
FIG. 8 is a diagram showing the derivation of a CHO cell line expressing tTA, CHO/A2, as described in the description of FIG. 7 above. In order to construct such a cell line, pZtTA is electroporated into CHO DUKX cells. After electroporation, 24 clones are selected in the presence of 1 µg/ml G418. These 24 clones are then transiently transfected with pTOP6 containing the CAT gene [pTOP6CAT]. The transfected clones are assayed for CAT activity. The level of activity is compared to that obtained by co-transfecting pTOP6CAT and pEDtTA into CHO cells and the cell line with highest CAT activity is selected.
Figure 9:
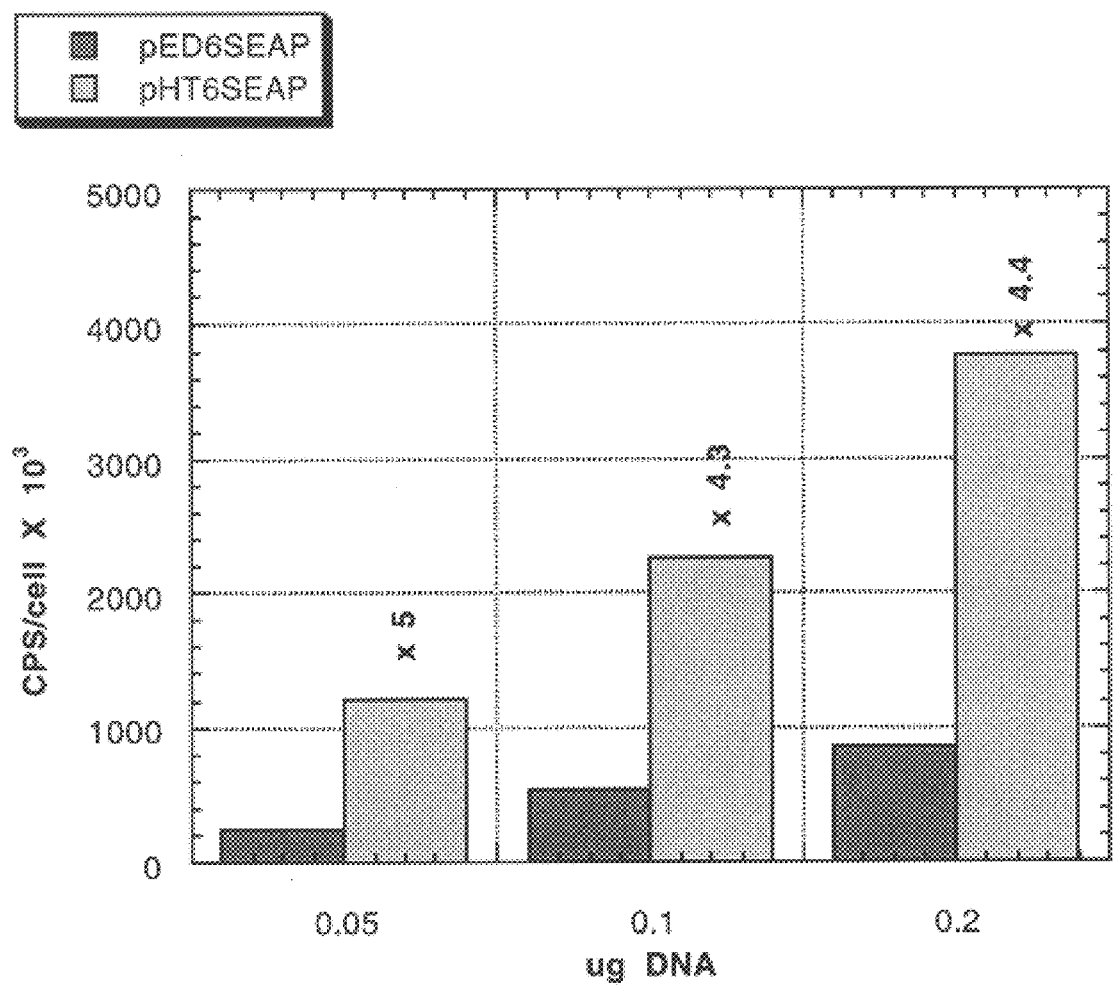
FIG. 9 is a graph showing the level of expression of the reporter gene secreted alkaline phosphatase (SEAP)

obtained from two vector, pEDSEAP and pHTOPSEAP. SEAP expression is monitored using a very sensitive chemiluminescent assay. 0.05, 0.1 and 0.2 ug of pEDSEAP and pHTOPSEAP were each lipofected into the CHO/A2 cell line. SEAP activity was determined in counts per second [CPS], which are proportional to SEAP activity in the range shown on the graph. In the transient transfection experiments shown in FIG. 9, the tet regulatable promoter is demonstrated to be approximately 5-fold stronger than the adenoviral major late promoter.

Figure 10:
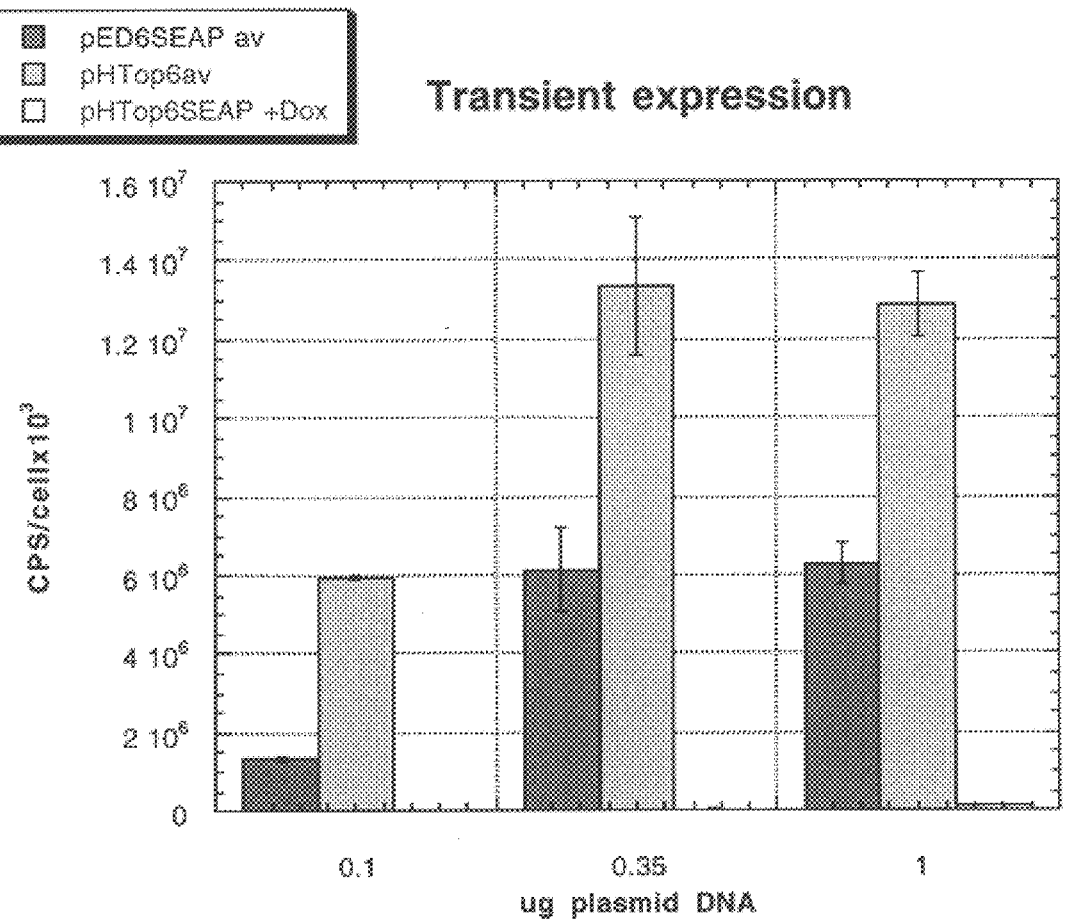

FIG. 10 is a graph showing the transient expression of SEAP in cells adenovirally transfected with pED6SEAP and pHTOP6SEAP, and pHTOP6SEAP in the presence of Doxycycline, an analog of tetracycline. Again, SEAP is shown to be expressed approximately 5-fold more strongly under the regulation of pHTOP6 than under pED6. Addition of Dox completely inhibits DNA expression by the tet promoter.

Figure 11:
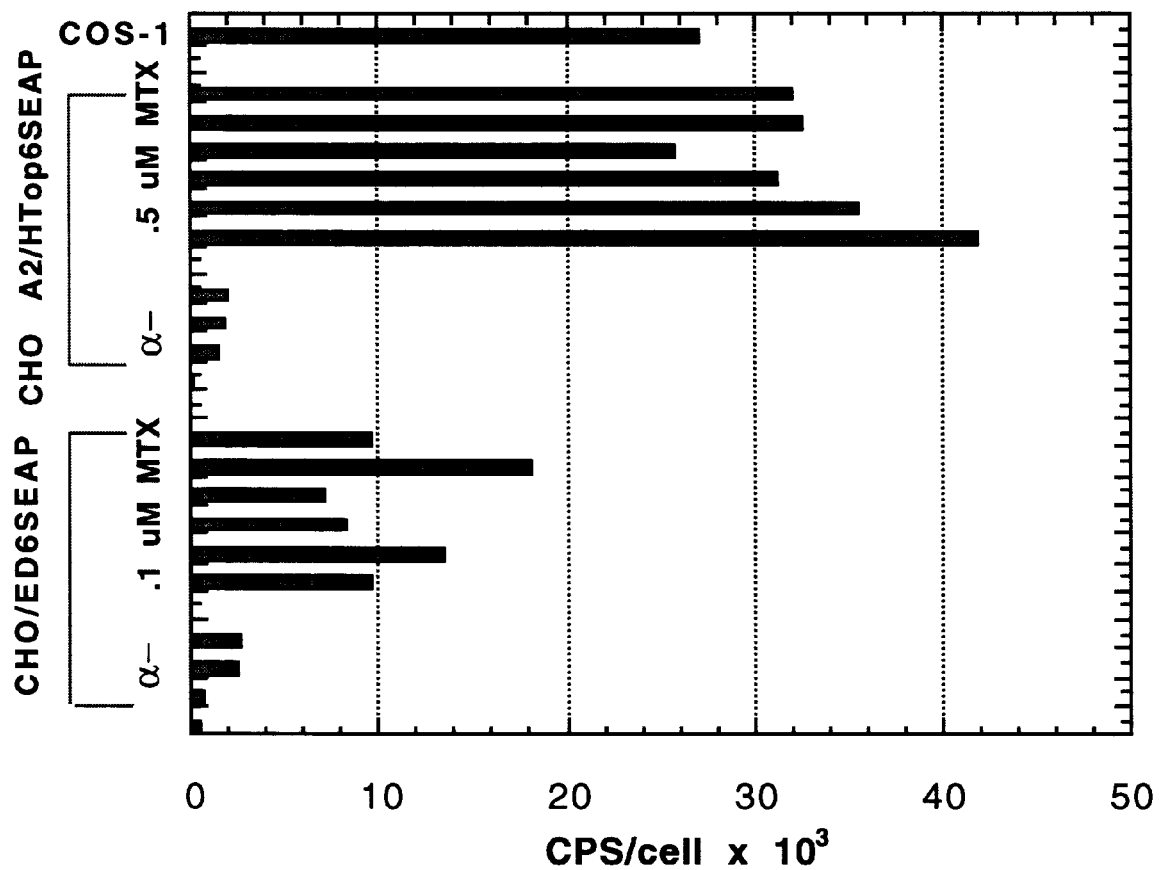

FIG. 11 is a graph comparing the level of stable expression of SEAP in CHO/A2 cell lines transfected with pED6SEAP and pHTOP6SEAP. Clones were picked in the highest MTX concentrations possible for each vector [0.1 uM MTX for CHO/ED6SEAP; 0.5 uM MTX for CHOA2/HTOP6SEAP]. The expression level observed in the concentration with MTX was about 30 fold higher than that observed in clones picked in alpha [no MTX]. The expression level in pHTOPSEAP is approximately 3-fold higher than that for pED6SEAP. The expression level in these clones is very high for CHO cell lines, as high as that obtained in COS-1 transient transfections.

FIG. 12 is a diagram of a streamlined protocol for one-step CHO cell line selection using the pHTOP vector and CHO/A2 transactivator cell line.

Figure 13:
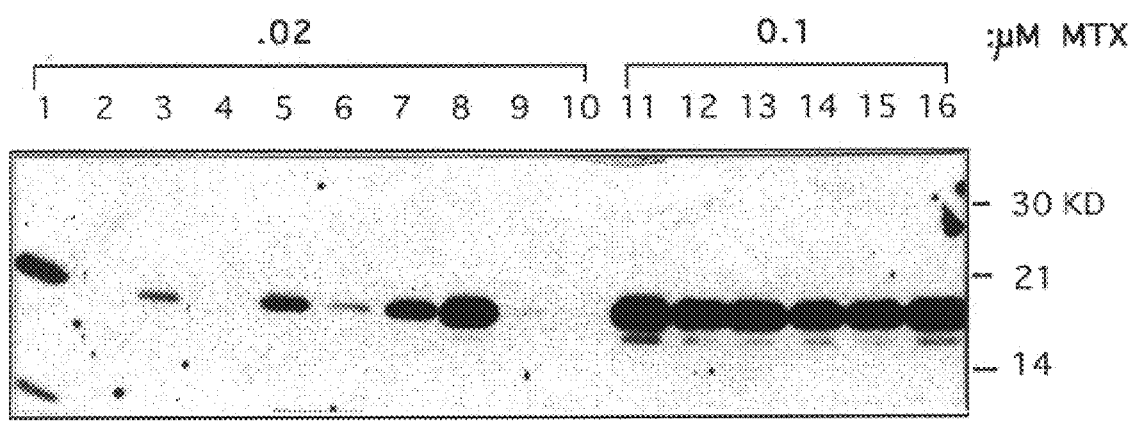

FIG. 13 is the Western blot analysis of CHO cells stably expressing hGDF-9, which were established by transfection using the pHTOP vector. 48 hours post-transfection, cells were plated for colony formation in 0.02 and 0.1 uM MTX. After two weeks, clones were picked from each MTX concentration. Cells were grown to confluence and 24 hour serum-free conditioned media was harvested for western analysis using a GDF-9 specific polyclonal antibody followed by chemiluminescent detection.

Clones selected in 0.1 uM MTX (lanes 11–16) expressed higher levels of GDF-9 compared with clones selected in 0.02 uM MTX (lanes 1–10). Clones selected in the lower MTX concentration displayed a wide range of expression. However GDF-9 expression levels were very uniform for clones selected in 0.1 uM MTX. Thus, stringent selection by increasing the concentration of methotrexate yields clones expressing uniformly high levels of protein.

FIG. 14 is a table demonstrating that the level of expression obtained with one-step selection varies from gene to gene. CHO cells which stably express secreted forms of mCD28, mB7.2 or mCTLA4 [all as mIgG2a fusion proteins) were established using the phTOP vector. Clones were selected in 0.05 uM MTX, grown to confluence and 24 hour serum-free conditioned media was harvested for mIgG2a ELISA. For the three genes expressed, mCTLA4 clones produced the highest protein levels [13 ug/ml] followed by mCD28 [8 ug/ml] and mB7.2 [3 ug/ml].

Figure 15:
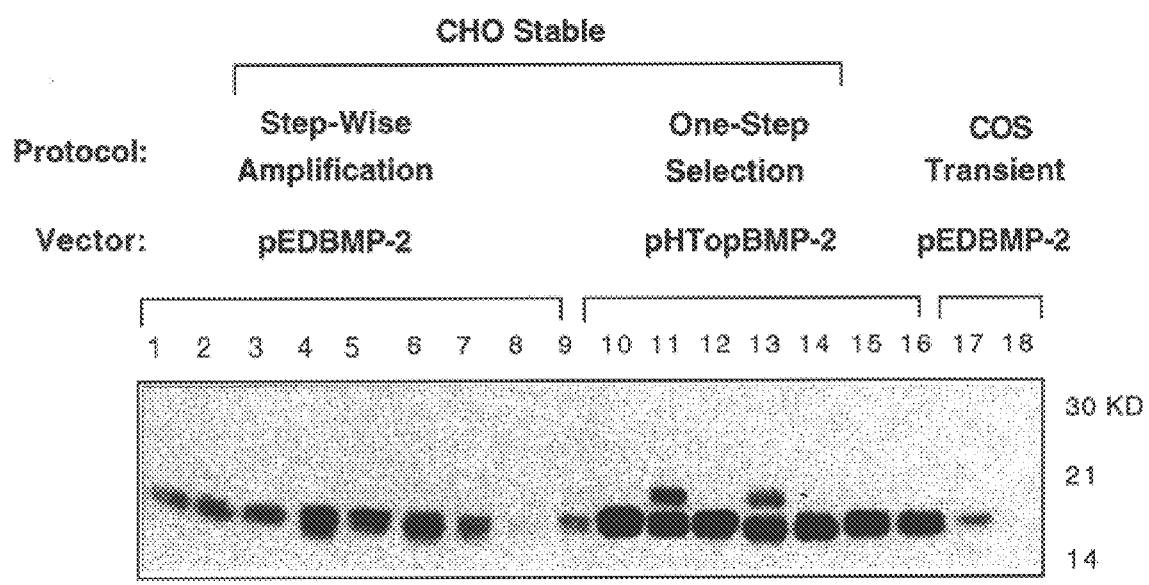

FIG. 15 is a Western Blot Analysis showing a comparison of mammalian expression systems. Lanes 1 through 9 show the effect of step-wise amplification of CHO cells stably transfected with pEDBMP-2. Lanes 10 through 16 show the effect of one-step selection of CHO cells stably stransfected with pHTOPBMP-2. Lanes 17 and 18 show COS transient transfection with pEDBMP-2 and a mock transfection.

DETAILED DESCRIPTION OF THE INVENTION

The vectors of the present invention make use of strong transcriptional elements activated by a chimeric transactivator construct stably expressed in a recipient mammalian cell line. In a preferred embodiment, the strong transcriptional elements comprise multiple copies of the tet operator positioned upstream and adjacent to a minimal mammalian "TATA" sequence. This combination forms a strong mammalian promoter. In a further preferred embodiment, this strong promoter directs the synthesis of a polycistronic message, in which expression of a resistance marker, such as the dihydrofolate resistance gene [DHFR], is linked to the expression of the gene of interest, allowing selection of highly expressing clones in a one-step selection process. In a preferred embodiment, a portion of a suitable leader sequence, such as the EMC virus [EMCV] leader, may be used for the efficient functioning of this polycistronic message. The EMCV leader sequence may be obtained, for example, from pMT2-ECAT1 [S. K. Jung, et al, *J. Virol* 63:1651–1660 (1989)]. The disclosure of this document is hereby incorporated herein by reference. The combined use of this strong chimera promoter, which produces a polycistronic message with a selectable resistance marker, with a host cell which expresses a chimeric transactivator, allows the rapid selection of cell lines producing high levels of recombinant protein in one step.

Secreted protein levels of up to approximately 50 ug/ml have been obtained using this one-step selection method. Clones stringently selected in high levels of methotrexate [MTX] produce uniform levels of protein, eliminating the need to screen large numbers of clones. Although the production level obtained with the initial selection step is variable from gene to gene, levels can be amplified by increasing the concentration of MTX. In addition, production levels are stable in the presence of selection or for at least 3 weeks when selection pressure is removed.

The present system has the advantage of developing stable cell lines much more rapidly than was previously possible using the usual step-wise amplification [approximately 1 month compared to approximately 4 months]. In addition, higher production levels can be obtained with this system compared to transient expression in COS cells. Accordingly, the present invention provides methods for developing high-expressing stable cell lines quickly and easily, filling the long-felt need for such systems between transient expression in COS cells [fast but labor intensive for large scale production of proteins] and stable expression by step-wise amplification [slow and labor intensive].

The expression system is based on the combined use of two elements: a chimeric transcription factor [tTA], which is a fusion between the *E. coli* tetracycline repressor [tet R] and the transcriptional domain of herpes simplex virus 16 (VP16), and a vector in which a minimal promoter providing a TATA box is preceded by multiple tet operator [tet O] sequences. These operators bring the strong activation domain of VP16 in close proximity to the basal transcription complex, activating it. This interaction can be reversed through the use of tetracycline, which can therefore be used as a switch to turn transcription "off." In the absence of tetracycline, expression is "on." However, the present method does not require that this regulation be used. Thus, in one embodiment, the present invention comprises a plasmid in which a minimal promoter is operably linked to a leader sequence which in turn is operably linked to a DHFR gene. Upstream of the leader sequence are one or more restriction sites suitable for the insertion of a gene encoding a desired protein for expression. In a preferred embodiment, the plasmid pHTOP6 is used, which is created from the plasmid pED as described further herein. The plasmid pHTOP is also useful in the present invention. In pHTOP, the junction between the EMCV leader and DHFR gene was altered to impair DHFR translation without affecting the level of expression of the upstream gene. For the production of larger proteins, where low levels of DHFR expression may be expected, pHTOP$^6$ may be the preferred vector. The methods of the present invention are useful for the production of both secreted and membrane proteins. The methods of this invention can be used as an alternative to large-scale COS transfections. In the preferred embodiment wherein CHO cells are used, the cells can be grown in serum-free media for the purification of proteins.

A transactivator cell line useful as a recipient mammalian cell line may be derived by transfecting a chimeric transcription factor, such as tTA described above, into suitable cell lines, such as a CHO cell line. In a preferred embodiment, the CHO cell line CHO DUKX B11, which is deficient in DHFR and therefore not normally able to survive in the presence of methotrexate selection, is used. A diagram of such a process is shown in FIGS. 10 and 11.

The plasmid pHTOP-X, where X is the coding sequence for the protein to be expressed is made and transfected into the transactivator cell line, and screened as illustrated in FIG. 15. Thus, in one embodiment, the present invention comprises recombinant DNA sequences comprising the DNA sequence of pHTOP or pHTOP6. In other embodiments, the present invention comprises methods for producing a stable recombinant mammalian cell line, said method comprising: (1) transfecting a recipient mammalian cell line with a plasmid vector to form a transfected recipient mammalian cell line, said plasmid vector comprising: (a) a minimal promoter preceded by multiple tet operators; (b) a leader sequence capable of directing the efficient expression of a polycistronic message; and (c) a polycistronic message comprising a first DNA encoding a protein of interest and a second DNA sequence encoding a selectable marker gene, and said recipient mammalian cell line comprising (1) a chimeric transcription factor, which comprises a fusion of one or more copies of an *E. Coli* tetracycline repressor; (2) a transcriptional domain of herpes simplex virus 16.; and (3) a vector comprising a minimal promoter preceded by multiple tet operator sequences; and (B) isolating the resulting said transfected recipient mammalian cell line. The transfected cell line may optionally be cultured for further use.

The examples below describe some of the preferred embodiments of the present invention.

A. In step-wise amplification, the following was observed CHO DUKX cells were stably transfected with pEDBMP-2. Cells were plated for colony formation in alpha nucleotide free media with 10% heat inactivated dialyzed FCS and 1 mg/ml G418 media 48 h post-transfection. After 2 weeks, clones were picked, grown in 0.02 $\mu$M MTX until stable (4 weeks) then transferred to 0.1 $\mu$M MTX and grown for 4 weeks. Serum-free conditioned media (24 h) was harvested from confluent cells for western analysis.

B. In the present one-step selection CHO DUKX/A2 cells were stably transfected with pHTOPBMP-2. 48 h post-transfection, cells were plated for colony formation in 0.1 M MTX and 1 mg/ml G418 media. Two weeks later, clones were picked, grown to confluence and serum-free conditioned media was harvested from confluent cells for western analysis.

C. COS transient transfections were accomplished using COS-1 cells transiently transfected with pEDBMP-2. 48–72 h post-transfection, serum-free conditioned media was harvested for western analysis.

Western analysis:

10 $\mu$M conditioned media from protocols A, B, C above were run on a 16% SDS-PAGE gel under reducing conditions and tranferred to nitrocellulose by western blot. BMP-2 was detected with a BMP-2 specific polyclonal antibody followed chemiluminescent detection.

Clones established by step-wise amplification using the pED vector displayed a wide range of BMP-2 expression. In contrast, clones picked in the one-step selection using the pHTop vector showed higher and more uniform BMP-2 expression. The level of BMP-2 expressed transiently in COS cells lane was much lower than that seen in the pHTop clones.

Stable CHO cell lines established using one-step selection displayed consistently higher expression levels compared with CHO step-wise amplification or COS transient. In addition, expression levels achieved with one-step selection were more uniform. CHO cell lines stably expressing a secreted form of a mB7. F-2mIgG2a fusion protein were established by transfection using the pHTop vector. Clones selected in 0.1 $\mu$M MTX were passaged twice a week in the presence or absence of selection (MTX and G418) for 3 weeks. Serum-free conditioned media (24 h) was harvested from confluent cells at 1, 2 and 3 weeks and analyzed by western blot using an anti-mIgG2a HRP antibody followed by chemiluminescent detection. Expression levels remained constant for at least 3 weeks when selection is removed from cells selected in high concentrations of methotrexate.

CHO cells stably expressing a secreted form of a hCD28-hIgG4 fusion protein were established by transfection using the pHTop vector. Clones were selected in 0.1 $\mu$M MTX, then grown in 0.5 $\mu$M MTX for 3 weeks. Serum-free conditioned media (24 h) harvested from confluent cells was analyzed by western blot using anti-hIgG-HRP antibody followed by chemiluminescent detection. Each lane represents 10 L conditioned media or purified hIgG4 protein for quantitation. Expression levels for conditioned media from the three highest expressing clones (2, 3, 5) were measured by hIgG4 ELISA.

Clones selected in 0.1 $\mu$M MTX express approximately 1–2 $\mu$g/ml hCD28/hIgG4 showed significant increase (5–10 fold) in hCD28 expression while 2 clones (#1,40 showed a moderate increase in expression. Expression levels of cells selected in high concentrations of methotrexate can be amplified by increasing the concentration of methotraxate.

CHO cell lines were established by transfecting pHTopmuFrzb-1 (murine Frazzled) and selecting clones in 0.05 $\mu$M MTX. 2 pools of colonies that survived 0.1 $\mu$M MTX were also established. Cells were labeled for 6 hr with 35S Methionine/Cysteine and conditioned media was harvested and analyzed by SDS-PAGE. Each lane represents 50 $\mu$l of conditioned media from clones and pools. Expression of individual clones selected in 0.05 $\mu$M MTX was uniform and the expression from the 2 pools was as high as that of the individual clones.

Due to the uniformity of expression of the individual clones under stringent selection conditions, it is possible to pool colonies without compromising expression, therefore speeding up the last step in the generation of stable cell lines.

CHO cell lines stably expressing CCR5 were established by transfection using the pHTop vector. Clones selected in 0.02 $\mu$M MTX were analyzed for CCR5 expression by FACS analysis. Transfected cells were stained using an anti-CCR5 monoclonal antibody (clone 45531.111 from R&D) or a murine IgG2a isotype for untransfected control cells followed by a PE-conjugated anti-murine IgG antibody. Of the 13 clones screened for CCR5 expression, 11 clones expressed CCR5 an demonstrated by a 2 log increase of fluorescence over untransfected control cells. Only 2 clones showed no CCR5 expression above background.

The one step selection system can also be used to express transmembrane proteins.

The examples and figures on the following pages illustrate practice of the present invention in generating stable mammalian cell lines which produce high levels of recombinant proteins, using cell lines and vectors which constitute part of the invention, which are suitable for use in such method. In the examples, it is demonstrated that the present invention is effective for the efficient production of recombinant proteins. A large number of modifications and variations will be apparent to the skilled artisan from reading this specification and the examples. Such modifications and variations constitute part of the invention, and the examples are not limiting.

What is claimed is:

1. A recombinant DNA sequence comprising the DNA sequence of pHTOP (SEQ ID No: 1).

2. A method for producing a stable recombinant Chinese Hamster Ovary (CHO) cell line, said method comprising:
(A) transfecting a CHO cell line with a first plasmid vector to form a stably transfected recipient CHO cell line, wherein said first plasmid vector encodes a chimeric transcription factor which comprises a fusion of an *E. coli* tetracycline repressor and a transcriptional activator domain of herpes simplex virus 16;

(B) transfecting the stably transfected recipient CHO cell line of step (A) with a second plasmid vector to form a stable recombinant CHO cell line, wherein said second plasmid vector comprises:
(a) a minimal promoter preceded by multiple tet operators;
(b) a leader sequence that directs the efficient expression of a polycistronic message wherein said polycistronic message comprises a first nucleotide sequence encoding a protein of interest and a second nucleotide sequence encoding a selectable dihydrofolate resistance (DHFR) marker gene; and (C) isolating and optionally culturing said stable recombinant CHO cell line.

3. An isolated DNA molecule for expressing a gene of interest in a mammalian cell line, the DNA molecule comprising:

(a) a minimal promoter operably linked to at least one tet operator sequence, (b) at least one restriction site suitable for inserting the gene of interest, (c) a leader sequence that directs the expression of a polycistronic message in the mammalian cell line, and (d) a selectable DHFR marker gene joined to the leader sequence at a junction; wherein the mammalian cell line comprises a chimeric transcription factor which comprises a fusion of an *E. Coli* tetracycline repressor and a transcriptional activator domain of a herpes simplex virus 16.

4. The isolated DNA molecule of claim 3, wherein the mammalian cell line is a Chinese Hamster Ovary (CHO) cell line.

5. The isolated DNA molecule of claim 4, wherein the CHO cell line is CHO DUKX B11.

6. The isolated DNA molecule of claim 3, wherein the leader sequence is the 5' nontranslated region of encephalomyocarditis virus (EMCV).

7. The isolated DNA molecule of claim 3, wherein the leader sequence is the 5' nontranslated region of encephalomyocarditis virus (EMCV) and wherein the junction between the EMCV leader sequence and the selectable DHFR marker gene has been altered by the insertion of a restriction site to impair DHFR translation without affecting the level of expression of the gene of interest.

8. The isolated DNA molecule of claim 3, wherein the minimal promoter comprises the TATA box and 35 base pairs of sequence upstream of the transcriptional start site derived from an adenovirus major late promoter (AdMLP) and an SV40 origin of replication.

9. The isolated DNA molecule of claim 3, wherein the gene of interest is a human gene.

10. The isolated DNA molecule of claim 3, wherein the gene of interest encodes a secreted or a membrane-bound protein.

11. The isolated DNA molecule of claim 3, wherein the gene of interest encodes a gene product selected from the group consisting of secreted alkaline phosphatase (SEAP), GDF-9, CD28, B7.2, CTLA4, bone morphogenetic protein 2 (BMP-2), Frazzled (Frzb-1), and CCR5 protein.

12. An isolated DNA molecule for expressing a gene of interest in a mammalian cell line, the DNA molecule comprising:

(a) a minimal promoter operably linked to at least one tet operator sequence, (b) a leader sequence that directs the the expression of a polycistronic message in the mammalian cell line, and (c) a polynucleotide sequence comprising the gene of interest and a selectable DHFR marker gene joined to the leader sequence at a junction;

wherein the polynucleotide sequence is operably linked to the leader sequence; and wherein the mammalian cell line comprises a chimeric transcription factor, the chimeric transcription factor comprising a prokaryotic tetracycline repressor operably linked to a polypeptide which activates transcription in eukaryotic cells.

13. The isolated DNA molecule of claim 12, wherein the mammalian cell line is a Chinese Hamster Ovary (CHO) cell line.

14. The isolated DNA molecule of claim 13, wherein the CHO cell line is CHO DUKX B11.

15. The isolated DNA molecule of claim 12, wherein the leader sequence is the 5' nontranslated region of encephalomyocarditis virus (EMCV).

16. The isolated DNA molecule of claim 12, wherein the gene of interest encodes a secreted or a membrane-bound protein.

17. The isolated DNA molecule of claim 12, wherein the gene of interest encodes a gene product selected from the group consisting of secreted alkaline phosphatase (SEAP), GDF-9, CD28, B7.2, CTLA4, bone morphogenetic protein 2 (BMP-2), Frazzled (Frzb-1), and CCR5 protein.

18. A transformed mammalian cell comprising the DNA molecule of claim 3.

19. A transformed mammalian cell comprising the DNA molecule of claim 12.

20. A method for selecting a transformed mammalian cell which produces a gene product encoded by a gene of interest, comprising:

(a) introducing the DNA molecule of claim 12 into a population of mammalian host cells;

(b) growing the mammalian host cells in a culture medium comprising methotrexate (MTX); and (c) selecting a mammalian cell which grows in the culture medium comprising MTX, wherein growth in said culture medium indicates that the mammalian cell is a transformed mammalian cell which produces the gene product encoded by the gene of interest.

21. A method for producing a protein product which comprises the steps of culturing a transformed mammalian cell of claim 18 in a culture medium comprising methotrexate (MTX) and under suitable conditions permitting the expression of the gene of interest, and recovering the protein product from the medium and the cells.

* * * * *

UNITED STATES PATENT AND TRADEMARK OFFICE
CERTIFICATE OF CORRECTION

PATENT NO. : 6,136,536
DATED : October 24, 2000
INVENTOR(S) : Kathleen Tomkinson et al.

Page 1 of 1

It is certified that error appears in the above-identified patent and that said Letters Patent is hereby corrected as shown below:

Title page,
FOREIGN PATENT DOCUMENTS, delete "wO 94/16075" and insert
-- WO 94/16075 --.

Column 3,
Line 47, delete "llowever" and insert -- However --.

Column 5,
Line 6, delete "(pllTOP)" and insert -- (pHTOP) --.
Line 10, delete "pHTOP⁶" and insert -- pHTOP6--.
Line 20, delete "CllO" and insert -- CHO --.

Column 6,
Line 33, delete "CllO" and insert -- CHO --.
Line 50, delete "CllO" and insert -- CHO --.

Column 11,
Line 59, delete "(pllTOP)" and insert -- (pHTOP) --.

Column 14,
Line 1, delete the first "the".

Signed and Sealed this

Twenty-ninth Day of January, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
  (A) LENGTH: 5639 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:1:

```
AAGCTCGAGC GCGGGACGTC CTTTGTTTAC GTCCCGTCGG CGCTGAATCC CGCGGACGAC      60

CCCTCTCGGG GCCGCTTGGG AGTCTCTCGT CCCCTTCTCC GTCTGCCGTT CCAGCCGACC     120

ACGGGGCGCA CCTCTCTTTA CGCGGTCTCC CCGTCTGTGC CTTCTCATCT GCCGGTCCGT     180

GTGCACTTCG CTTCACCTCT GCACGTTGCA TGGAGACCAC CGTGAACGCC CATCAGATCC     240

TGCCCAAGGT CTTACATAAG AGGACTCTTG GACTCTCAGC AATGTCAACG ACCGACCTTG     300

AGGCCTACTT CAAAGACTGT GTGTTTAAGG ACTGGGAGGA GCTGGGGGAG GAGATTAGGT     360

TAAAGGTCTT TGTATTAGGA GGCTGTAGGC ATAAATTGGT CTGCGCACCA GCACCATGCA     420

ACTTTTTCAC CTCTGCCTAA TCATCTCTTG TACATGTCCC ACTGTTCAAG CCTCCAAGCT     480

GTGCCTTGGG TGGCTTTGGG GCATGGACAT TGACCCTTAT AAAGAATTTG GAGCTACTGT     540

GGAGTTACTC TCGTTTTTGC CTTCTGACTT CTTTCCTTCC GTCAGCTCGA GTTTACCACT     600

CCCTATCAGT GATAGAGAAA AGTGAAAGTC GAGTTTACCA CTCCCTATCA GTGATAGAGA     660

AAAGTGAAAG TCGAGGTCGA GTTTACCACT CCCTATCAGT GATAGAGAAA AGTGAAAGTC     720

GAGGTCGAGT TTACCACTCC CTATCAGTGA TAGAGAAAAG TGAAAGTCGA GTTTACCACT     780

CCCTATCAGT GATAGAGAAA AGTGAAAGTC GAGGTCGAGT TTACCACTCC CTATCAGTGA     840

TAGAAAAGTG AAAGTGAAAG TCGAGGTCGA GTCGAGGGGG GCTATAAAAG GGGGTGGGGG     900

CGCGTTCGTC CTCACTCTCT TCCGCATCGC TGTCTGCGAG GGCCAGCTGT TGGGCTCGCG     960

GTTGAGGACA AACTCTTCGC GGTCTTTCCA GTACTCTTGG ATCGGAAACC CGTCGGCCTC    1020

CGAACGGTAC TCCGCCACCG AGGGACCTGA GCGAGTCCGC ATCGACCGGA TCGGAAAACC    1080

TCTCGACTGT TGGGGTGAGT ACTCCCTCTC AAAAGCGGGC ATGACTTCTG CGCTAAGATT    1140

GTCAGTTTCC AAAAACGAGG AGGATTTGAT ATTCACCTGG CCCGCGGTGA TGCCTTTGAG    1200

GGTGGCCGCG TCCATCTGGT CAGAAAAGAC AATCTTTTTG TTGTCAAGCT TGAGGTGTGG    1260

CAGGCTTGAG ATCTGGCCAT ACACTTGAGT GACAATGACA TCCACTTTGC CTTTCTCTCC    1320
```

-continued

```
ACAGGTGTCC ACTCCCAGGT CCAACTGCAG GTCGACTCTA GACCCGGGGA ATTCTAACGT      1380

TACTGGCCGA AGCCGCTTGG AATAAGGCCG GTGTGCGTTT GTCTATATGT TATTTTCCAC      1440

CATATTGCCG TCTTTTGGCA ATGTGAGGGC CCGGAAACCT GGCCCTGTCT TCTTGACGAG      1500

CATTCCTAGG GGTCTTTCCC CTCTCGCCAA AGGAATGCAA GGTCTGTTGA ATGTCGTGAA      1560

GGAAGCAGTT CCTCTGGAAG CTTCTTGAAG ACAAACAACG TCTGTAGCGA CCCTTTGCAG      1620

GCAGCGGAAC CCCCCACCTG GCGACAGGTG CCTCTGCGGC CAAAAGCCAC GTGTATAAGA      1680

TACACCTGCA AAGGCGGCAC AACCCCAGTG CCACGTTGTG AGTTGGATAG TTGTGGAAAG      1740

AGTCAAATGG CTCTCCTCAA GCGTATTCAA CAAGGGCTG AAGGATGCCC AGAAGGTACC       1800

CCATTGTATG GGATCTGATC TGGGGCCTCG GTGCACATGC TTTACATGTG TTTAGTCGAG      1860

GTTAAAAAAC GTCTAGGCCC CCCGAACCAC GGGGACGTGG TTTTCCTTTG AAAAACACGA      1920

TTGCTCGAGC CATCATGGTT CGACCATTGA ACTGCATCGT CGCCGTGTCC CAAAATATGG      1980

GGATTGGCAA GAACGGAGAC CTACCCTGGC CTCCGCTCAG GAACGAGTTC AAGTACTTCC      2040

AAAGAATGAC CACAACCTCT TCAGTGGAAG GTAAACAGAA TCTGGTGATT ATGGGTAGGA      2100

AAACCTGGTT CTCCATTCCT GAGAAGAATC GACCTTTAAA GGACAGAATT AATATAGTTC      2160

TCAGTAGAGA ACTCAAAGAA CCACCACGAG GAGCTCATTT TCTTGCCAAA AGTTTGGATG      2220

ATGCCTTAAG ACTTATTGAA CAACCGGAAT TGGCAAGTAA AGTAGACATG GTTTGGATAG      2280

TCGGAGGCAG TTCTGTTTAC CAGGAAGCCA TGAATCAACC AGGCCACCTC AGACTCTTTG      2340

TGACAAGGAT CATGCAGGAA TTTGAAAGTG ACACGTTTTT CCCAGAAATT GATTTGGGGA      2400

AATATAAACT TCTCCCAGAA TACCCAGGCG TCCTCTCTGA GGTCCAGGAG GAAAAAGGCA      2460

TCAAGTATAA GTTTGAAGTC TACGAGAAGA AAGACTAACA GGAAGATGCT TTCAAGTTCT      2520

CTGCTCCCCT CCTAAAGCTA TGCATTTTTT ATAAGACCAT GGGACTTTTG CTGGCTTTAG      2580

ATCATAATCA GCCATACCAC ATTTGTAGAG GTTTTACTTG CTTTAAAAAA CCTCCCACAC      2640

CTCCCCCTGA ACCTGAAACA TAAAATGAAT GCAATTGTTG TTGTTAACTT GTTTATTGCA      2700

GCTTATAATG GTTACAAATA AAGCAATAGC ATCACAAATT TCACAAATAA AGCATTTTTT      2760

TCACTGCATT CTAGTTGTGG TTTGTCCAAA CTCATCAATG TATCTTATCA TGTCTGGATC      2820

CCCGGCCAAC GGTCTGGTGA CCCGGCTGCG AGAGCTCGGT GTACCTGAGA CGCGAGTAAG      2880

CCCTTGAGTC AAAGACGTAG TCGTTGCAAG TCCGCACCAG GTACTGATCA TCGATGCTAG      2940

ACCGTGCAAA AGGAGAGCCT GTAAGCGGGC ACTCTTCCGT GGTCTGGTGG ATAAATTCGC      3000

AAGGGTATCA TGGCGGACGA CCGGGGTTCG AACCCCGGAT CCGGCCGTCC GCCGTGATCC      3060

ATCCGGTTAC CGCCCGCGTG TCGAACCCAG GTGTGCGACG TCAGACAACG GGGGAGCGCT      3120

CCTTTTGGCT TCCTTCCAGG CGCGGCGGCT GCTGCGCTAG CTTTTTTGGC GAGCTCGAAT      3180

TAATTCTGCA TTAATGAATC GGCCAACGCG CGGGGAGAGG CGGTTTGCGT ATTGGGCGCT      3240

CTTCCGCTTC CTCGCTCACT GACTCGCTGC GCTCGGTCGT TCGGCTGCGG CGAGCGGTAT      3300

CAGCTCACTC AAAGGCGGTA ATACGGTTAT CCACAGAATC AGGGGATAAC GCAGGAAAGA      3360

ACATGTGAGC AAAAGGCCAG CAAAAGGCCA GGAACCGTAA AAAGGCCGCG TTGCTGGCGT      3420

TTTTCCATAG GCTCCGCCCC CCTGACGAGC ATCACAAAAA TCGACGCTCA AGTCAGAGGT      3480

GGCGAAACCC GACAGGACTA TAAAGATACC AGGCGTTTCC CCCTGGAAGC TCCCTCGTGC      3540

GCTCTCCTGT TCCGACCCTG CCGCTTACCG GATACCTGTC CGCCTTTCTC CCTTCGGGAA      3600

GCGTGGCGCT TTCTCAATGC TCACGCTGTA GGTATCTCAG TTCGGTGTAG GTCGTTCGCT      3660

CCAAGCTGGG CTGTGTGCAC GAACCCCCCG TTCAGCCCGA CCGCTGCGCC TTATCCGGTA      3720
```

```
ACTATCGTCT TGAGTCCAAC CCGGTAAGAC ACGACTTATC GCCACTGGCA GCAGCCACTG    3780

GTAACAGGAT TAGCAGAGCG AGGTATGTAG GCGGTGCTAC AGAGTTCTTG AAGTGGTGGC    3840

CTAACTACGG CTACACTAGA AGGACAGTAT TTGGTATCTG CGCTCTGCTG AAGCCAGTTA    3900

CCTTCGGAAA AAGAGTTGGT AGCTCTTGAT CCGGCAAACA AACCACCGCT GGTAGCGGTG    3960

GTTTTTTTGT TTGCAAGCAG CAGATTACGC GCAGAAAAAA AGGATCTCAA GAAGATCCTT    4020

TGATCTTTTC TACGGGGTCT GACGCTCAGT GGAACGAAAA CTCACGTTAA GGGATTTTGG    4080

TCATGAGATT ATCAAAAAGG ATCTTCACCT AGATCCTTTT AAATTAAAAA TGAAGTTTTA    4140

AATCAATCTA AAGTATATAT GAGTAAACTT GGTCTGACAG TTACCAATGC TTAATCAGTG    4200

AGGCACCTAT CTCAGCGATC TGTCTATTTC GTTCATCCAT AGTTGCCTGA CTCCCCGTCG    4260

TGTAGATAAC TACGATACGG GAGGGCTTAC CATCTGGCCC CAGTGCTGCA ATGATACCGC    4320

GAGACCCACG CTCACCGGCT CCAGATTTAT CAGCAATAAA CCAGCCAGCC GGAAGGGCCG    4380

AGCGCAGAAG TGGTCCTGCA ACTTTATCCG CCTCCATCCA GTCTATTAAT TGTTGCCGGG    4440

AAGCTAGAGT AAGTAGTTCG CCAGTTAATA GTTTGCGCAA CGTTGTTGCC ATTGCTACAG    4500

GCATCGTGGT GTCACGCTCG TCGTTTGGTA TGGCTTCATT CAGCTCCGGT TCCCAACGAT    4560

CAAGGCGAGT TACATGATCC CCCATGTTGT GCAAAAAAGC GGTTAGCTCC TTCGGTCCTC    4620

CGATCGTTGT CAGAAGTAAG TTGGCCGCAG TGTTATCACT CATGGTTATG GCAGCACTGC    4680

ATAATTCTCT TACTGTCATG CCATCCGTAA GATGCTTTTC TGTGACTGGT GAGTACTCAA    4740

CCAAGTCATT CTGAGAATAG TGTATGCGGC GACCGAGTTG CTCTTGCCCG GCGTCAATAC    4800

GGGATAATAC CGCGCCACAT AGCAGAACTT TAAAAGTGCT CATCATTGGA AAACGTTCTT    4860

CGGGGCGAAA ACTCTCAAGG ATCTTACCGC TGTTGAGATC CAGTTCGATG TAACCCACTC    4920

GTGCACCCAA CTGATCTTCA GCATCTTTTA CTTTCACCAG CGTTTCTGGG TGAGCAAAAA    4980

CAGGAAGGCA AAATGCCGCA AAAAAGGGAA TAAGGGCGAC ACGGAAATGT TGAATACTCA    5040

TACTCTTCCT TTTTCAATAT TATTGAAGCA TTTATCAGGG TTATTGTCTC ATGAGCGGAT    5100

ACATATTTGA ATGTATTTAG AAAAATAAAC AAATAGGGGT TCCGCGCACA TTTCCCCGAA    5160

AAGTGCCACC TGACGTCTAA GAAACCATTA TTATCATGAC ATTAACCTAT AAAAATAGGC    5220

GTATCACGAG GCCCTTTCGT CTCGCGCGTT TCGGTGATGA CGGTGAAAAC CTCTGACACA    5280

TGCAGCTCCC GGAGACGGTC ACAGCTTGTC TGTAAGCGGA TGCCGGGAGC AGACAAGCCC    5340

GTCAGGGCGC GTCAGCGGGT GTTGGCGGGT GTCGGGCTG GCTTAACTAT GCGGCATCAG    5400

AGCAGATTGT ACTGAGAGTG CACCATATGC GGTGTGAAAT ACCGCACAGA TGCGTAAGGA    5460

GAAAATACCG CATCAGGCGC CATTCGCCAT TCAGGCTGCG CAACTGTTGG GAAGGGCGAT    5520

CGGTGCGGGC CTCTTCGCTA TTACGCCAGC TGGCGAAAGG GGGATGTGCT GCAAGGCGAT    5580

TAAGTTGGGT AACGCCAGGG TTTTCCCAGT CACGACGTTG TAAAACGACG GCCAGTGCC    5639
```